US00PP09049P

United States Patent [19]

Hoff

[11] Patent Number: Plant 9,049

[45] Date of Patent: Jan. 31, 1995

[54] VARIETY OF LILIUM NAMED HOLEAW

[75] Inventor: Petrus M. M. Hoff, Steenbergen, Netherlands

[73] Assignee: Hoffgaarde B.V., Steenbergen, Netherlands

[21] Appl. No.: 177,193

[22] Filed: Jan. 4, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Webb Ziesenheim Bruening Logsdon Orkin & Hanson

[57] ABSTRACT

A new and distinct cultivar of lily plant named Holeaw, particularly characterized by greyish-purple flowers, height of about 120 cm, pedicel 10–12 cm long with 4–6 flowers, narrow leaves, and capable of producing stems and flowers for cut-flower production.

1 Drawing Sheet

BACKGROUND OF THE INVENTION

The present invention comprises a new and distinct cultivar of lily, botanically known as Lilium asiatic and hereinafter referred to by the cultivar name Holeaw.

The new cultivar is a product of a planned breeding program which had the objectives of creating new lily cultivars with the capacity to produce stems and flowers for cut-flower production.

The new cultivar was originated from a hybridization made by the inventor Messr. Petrus Mattheus Maria Hoff in a controlled breeding program at Hoffgaarde, B.V., Franseweg 9, 4651 PV Steenbergen, The Netherlands in 1988. The female and male parents were seedlings originated by Applicant, which were proprietary, and maintained by Applicant for breeding purposes.

The new cultivar was discovered and selected as one flowering plant within the progeny of the stated cross by the inventor on May 1, 1990 in a controlled environment in Steenbergen.

The first act of asexual reproduction of the new cultivar was accomplished by the inventor when scales were taken from the initial selection on Oct. 24, 1990 in a controlled environment in Steenbergen.

Horticultural examination of selected units initiated Apr. 20, 1991 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commercial practice.

The following traits have been repeatedly observed and are determined to be basic characteristics of the new cultivar which in combination distinguish this lily as a new and distinct cultivar.

(1) Color of the flowers (greyish-purple).

(2) About 120 cm in height.

(3) Pedicel 10–12 cm in length with 4–6 flowers.

(4) Narrow leaves.

The accompanying color photographic drawing shows typically flower characteristics of the new cultivar, with colors being as true as possible with illustrations of this type. In the following description, color references are made to the Royal Horticultural Society Colour Chart. The color values were determined at Steenbergen on Apr. 20, 1991.

THE PLANT

Classification:

*Botanic.*—*Lilium asiatic.*

*Commercial.*—Hybrid asiatic lily for cut flower production.

Form: Single upright stem from each bulb.

Height: About 120 cm.

Growth habit: Upright, erect, strong and rigorous.

Stem:

*Diameter.*—1.2 cm average.

*Color.*—Green Group 137A.

*Form.*—Rounded.

Foilage:

*Quantity.*—75–90 leaves.

*Size of leaf.*—About 10 cm long, 0.9 cm wide up to about 14 cm long, 2.2 cm wide.

*Shape of leaf.*—Elliptic.

*Texture of leaf.*—Smooth.

*Color.*—Green Group 136A.

Bulbs:

*Size.*—12–14 cm in circumference.

*Color.*—Pinkish-red and white.

THE BUD

Form: Oblong, diamond (UPOV Type VII).

Size: 12 cm in length.

Color: Greyed-Purple Group 187A.

THE FLOWER

Blooming habit: 85 days after planting.

Size: 16 cm in diameter.

Borne: Umbellate single.

Shape: Narrow acute (UPOV Type II).

Tepalage:

*Number of tepals.*—6.

*Arrangement.*—Hexagonal, inner tepals barely covering outer tepals.

*Color (inner and outer tepals).*—Upper surface: Greyed-Purple Group 187A. Lower surface: Greyed-Purple Group 187A.

*Effect of temperature.*—Higher temperture lightens color to 187B–187D.

*Spotting.*—On inner and outer tepals, color slightly darker than tepal base color.

Pedicel:

*Length.*—14 cm.

*Color.*—Dark green with anthocyanin coloring.

*Form.*—Upright.

Texture: Velvety.

Nectaries:

*Size.*—1 cm.

*Color.*—Greyed-Purple Group 187A.

Disease resistance: No unusual disease problems have been observed.

Fragrance: None.

Lasting quality: 11 days in water after cutting.

REPRODUCTIVE ORGANS

Stamens:

*Number.*—6.

*Length.*—7 cm.

*Anthers — color.*—Purplish-brown.

*Pollen — color.*—Purplish-brown.

*Filaments — color.*—Purple.

Pistils: One, medium length.

Stigma:

*Color.*—Purple.

Ovaries:

*Color.*—Green.

I claim:

1. A new and distinct variety of lily plant substantially as shown and descibed.

* * * * *

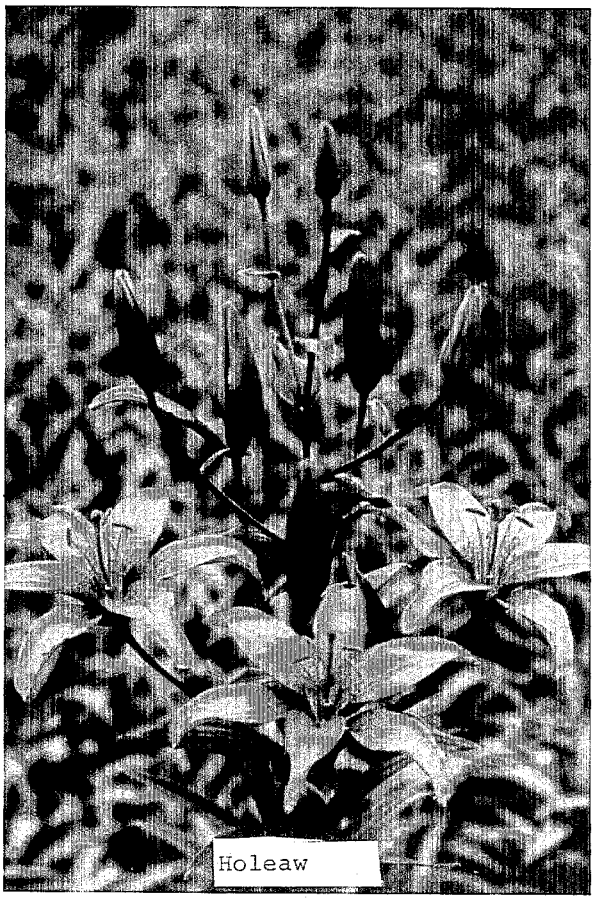
Holeaw